(12) United States Patent
Makulska

(10) Patent No.: US 10,473,651 B2
(45) Date of Patent: Nov. 12, 2019

(54) METHOD FOR DETERMINING AGGLUTINATION

(71) Applicants: Geomobile Sp. z o.o., Lodz (PL); Sylwia Makulska, Lesznowola (PL)

(72) Inventor: Sylwia Makulska, Lesznowola (PL)

(73) Assignees: Geomobile Sp. z o.o, Lodz (PL); Sylwia Makulska, Lesznowola (PL)

( * ) Notice: Subject to any disclaimer, the term of this patent is extended or adjusted under 35 U.S.C. 154(b) by 883 days.

(21) Appl. No.: 14/953,357

(22) Filed: Nov. 29, 2015

(65) Prior Publication Data
US 2016/0153971 A1 Jun. 2, 2016

(30) Foreign Application Priority Data
Nov. 28, 2014 (EP) ..................................... 14461594

(51) Int. Cl.
| | | |
|---|---|---|
| *G01N 33/53* | (2006.01) | |
| *G01N 33/49* | (2006.01) | |
| *B01L 3/00* | (2006.01) | |

(52) U.S. Cl.
CPC .... *G01N 33/5304* (2013.01); *B01L 3/502746* (2013.01); *G01N 33/4905* (2013.01); *B01L 2200/0673* (2013.01); *B01L 2200/148* (2013.01)

(58) Field of Classification Search
None
See application file for complete search history.

(56) References Cited

FOREIGN PATENT DOCUMENTS

FR  2991457  12/2013

OTHER PUBLICATIONS

Boedicker et al., Detecting bacteria and determining their susceptibility to antibiotics by stochastic confinement in nanoliter droplets using plug-based microfluidics, Lab Chip, 2008, 8, 1265-1272 (Year: 2008).*
Vanapalli et al., Hydrodynamic resistance of single confined moving drops in rectangular microchannels, Lab Chip, 2009, 9, 982-990. (Year: 2009).*
Sylwia Makulska,t Slawomir Jakielat and Piotr Garstecki; "A micro-rheological method for determination of blood type", in Lab Chip, 2013, 13, 2796-2801.

* cited by examiner

*Primary Examiner* — Andrea S Grossman
(74) *Attorney, Agent, or Firm* — Mark M. Friedman

(57) ABSTRACT

A method for determining agglutination of a biological liquid by measuring a change in hydrodynamic resistance of the biological liquid flowing through a microfluidic channel of a microfluidic device, comprising the steps of: a) calibrating the microfluidic device; b) filling the microfluidic reaction channel with a hydrophobic continuous liquid phase, c) introducing a first reference droplet; d) causing the first reference droplet to flow; e) measuring the time of flow of the first reference droplet; f) introducing a second reference droplet followed by a sequence of test droplet(s); g) causing the second reference droplet and the sequence of test droplet(s) to flow; h) measuring the time of flow; i) calculating the hydrodynamic resistance of the sequence of the test droplet(s); and j) determining agglutination of the biological liquid by comparing the hydrodynamic resistance with the calibrated values.

9 Claims, 3 Drawing Sheets

METHOD FOR DETERMINING AGGLUTINATION

TECHNICAL FIELD

The present invention relates to a method for performing agglutination tests of biological fluids such as blood or its components, or saliva or urine, and more generally for determining antigen-antibody reactions involving agglutination, in microfluidic devices.

BACKGROUND

Lab-on-chips, usually operating as microfluidic devices, are constructs that facilitate a variety of assays of biological liquid samples, e.g. blood, blood plasma or urine. Nowadays, microfluidic systems are becoming of increased importance as they require reduced sample usage to be investigated due to their miniaturization.

One of the assays that have been applied to microfluidic systems includes agglutination tests of blood. Typically, the measurement involves a reaction of the blood cells or the whole blood with the substance acting as a reagent, i.e. an agglutination agent (antibody), within channel(s) (such as microfluidic channel(s)), wherein the reagent causes a change in certain physical properties of the investigated blood, so that the agglutination may be determined by measuring the change. Typically, blood typing is performed with the use of blood fractions, i.e. after centrifugation. Blood cells isolated from the whole blood are then tested in contact with monoclonal reagents containing antibodies, and isolated plasma is tested with standardized red blood cells with known antigens on their surface.

Another category of serological tests are immunoassays, such as PCR and ELISA.

The most widely known methods for determining agglutination involve visual assessment of clumping of blood cells in the sample, which can be conducted either in a large scale, e.g. on glass plates and in test tubes, or in miniaturized scale with microfluidic systems.

For example, the U.S. Pat. No. 8,318,439 describes a microfluidic apparatus for blood typing by visual determination of appearance of the aggregates resulting in agglutination process. The device comprises an agglutination reaction channel provided with blood supply, an agglutination reagent supply, a throat and an optical window wherein the positive reaction may be optically assessed by appearance of "clumps" which are visible in the window. Further, the selected dimensions of the throat influence on the Reynolds number, and therefore potentiate the agglutination reaction. Nevertheless, the visual method may cause generation of errors due to the imperfections of human eye.

In addition, various other documents describe devices and methods for determining agglutination of the biological liquid samples by comparison of change in blood viscosity.

For instance, a PCT patent application WO2012164263 describes a microfluidic system and an assay method, which involve measuring a variation in viscosity of a sample. The microfluidic device consists of two parallel channels intersected at their inlets and outlets. The method involves adding blood sample into the microfluidic channels followed by providing a chase buffer into the channel. The liquid flows along the first and the second channel, wherein the agglutination agent is provided in the first, but not in the second channel. As the agglutination slows the flow rate of the blood sample, only non-agglutinated fluid may fall out of the channels arrangement, and thus block the agglutinated sample in the first channel. The distance travelled by the agglutinated liquid in the first channel is indicative of the degree of agglutination.

A similar method and device are described in a US patent application US20090317793. The device comprises a reference channel and a test channel in which an agglutination agent is provided. The channels are intersected at their both ends and provided with merging regions arranged such that the reference liquid flowing from the upper reference channel section into the merging region blocks a test liquid flow in the upper test channel. The agglutination is determined visually by observation of the position of flow of front of the sample liquid in the test channel.

Another diagnostic assay method is described in a PCT patent application WO2011035385. The method involves agglutination of a sample, followed by its deposition on a porous analytical substrate, on which the sample wicks. The sample that agglutinated upon contact with the specific antibodies separates/elutes upon contact with the substrate, while the blood sample upon contact with non-specific antibody does not separate/elute. The elution velocity and the extent of sample separation on the substrate indicate the coagulation degree.

A US patent application US20030224457 describes a method for determining the presence of antibodies in a blood sample by reverse typing on an optical bio-disc provided with a microfluidic channel; the method involves applying a blood sample into the microfluidic channel followed by spinning a disc which effects on movement of a blood serum through the microfluidic channel; next, adding to the serum a known ABO blood group and spinning the optical bio-disc, then incubating the mixture within the microfluidic channel. The agglutination is measured by scanning the mixture with an incident beam of electromagnetic radiation. Data obtained by irradiation determines the presence of agglutinated cells.

Thus, there are numerous ways to determine agglutination with microfluidic devices. However, in certain circumstances, the agglutination reaction may cause a cessation of flow and thus, the sample may be blocked, which may further lead to erroneous estimation of the agglutination assay income. In addition, it may cause difficulties in cleaning of the microfluidic channels. Moreover, when using a smaller sample, i.e. a sample having a size of a droplet or a droplet, or in case when agglutination reaction degree is substantially meager, typically, the agglutination phenomenon might not be assessed correctly.

A polish patent application PL396494 describes a device and a method for conducting agglutination test with a microfluidic system using a droplet size blood sample. The microfluidic system is provided with an antibody carrier droplet (such as monoclonal reagents) supply, an antigen carrier droplet (e.g. red blood cells) supply and a microfluidic channel in which the substances are mixed. The assay involves measuring the time of flow of the droplet at a predetermined distance along the microfluidic channel. The time of flow of the droplet, for which the agglutination reaction occurred, is significantly longer than the analogous time for droplet for which no reaction occurred; the comparison of the times of flow allows to distinguish whether the agglutination occurred or not.

Thus, there exists a need for further development of measurement of the changes in physical properties of liquids when flowing through microfluidic channels. Various methods have been described to address this need. For example, the following methods have been proposed for measuring of additional resistance of droplets in microfluidic channels:

V. Labrot et al., *Biomicrofluidics*, vol. 3, p. 012804, 2009, describes a method for direct measuring of the pressure droplet on a short section of a channel during the flow of a single droplet. Nonetheless, it requires the use of a very precise micromanometer and causes additional errors due to the presence of side channels for measuring the pressure.

Another method, described in S. A. Vanapalli et al., *Lab on a Chip*, vol. 9, p. 982, 2009, features a flow comparator based on balancing the measured flow (with droplet) with a dyed reference flow of controlled rate. Nonetheless, the quality of this method is limited by the experimental indication of the displacement of interface between dyed and clear oil.

Yet another known method, described in M. J. Fuerstman et al., *Lab on a Chip*, vol. 7, p. 1479, 2007 and V. Labrot et al., *Biomicrofluidics*, vol. 3, p. 012804, 2009 utilizes the model of flow of discrete segments of fluids through a simple loop of channels by measuring the velocity of flow of bubbles or droplets. The accuracy of this method depends critically on a number of assumptions and technical details: the behavior of droplets at diverging junctions and the spatial resolution of the measurements.

The methods quoted above are based on observations and measurements of properties of individual droplets.

It follows from the above-mentioned publications that the techniques of measurement of the change in certain physical properties of liquid samples with the microfluidic channels undergo fast development.

There exists a need for further development of agglutination test methods based on measurement of change in physical properties of a liquid sample, which will be more efficient and will lead to more reliable results, even whilst providing reduced sample size, such as droplets.

SUMMARY

A method for determining agglutination of a biological liquid by measuring a change in hydrodynamic resistance of the biological liquid flowing through a microfluidic channel of a microfluidic device, the method comprising the steps of: a) calibrating the microfluidic device by calculating a calibrated value of hydrodynamic resistance of a sequence of droplets of a known biological liquid in which agglutination occurred and a calibrated value of a sequence of droplets of a known biological liquid in which agglutination did not occur, according to steps—which are then performed for a tested biological liquid; b) filling the microfluidic reaction channel with a hydrophobic continuous liquid phase, the microfluidic reaction channel having detectors (6, 7) spaced at the distance defining measurement section of the microfluidic reaction channel; c) introducing into the microfluidic reaction channel a first reference droplet being a droplet of the biological liquid merged with saline or PBS or water and immiscible with the continuous phase; d) causing the first reference droplet to flow through the microfluidic reaction channel having a measurement section; e) measuring the time of flow of the first reference droplet through the measurement section of the microfluidic reaction channel; f) introducing into the microfluidic reaction channel a second reference droplet being the same as the first reference droplet, followed by a sequence of 1 to 1000 test droplet, the test droplet being droplet of the biological liquid, the same as comprised in reference droplets, and the agglutination reagent and immiscible with continuous phase; g) causing the second reference droplet and the sequence of test droplet to flow through the microfluidic reaction channel; h) measuring the time of flow of the second reference droplet through the measurement section at the presence of the sequence of test droplet in the microfluidic reaction channel; i) calculating the hydrodynamic resistance of the sequence of the test droplet; and j) determining agglutination of the biological liquid by comparing the hydrodynamic resistance with the calibrated values.

The continuous phase may separate the droplet from the microfluidic channel wall surface.

The biological liquid can be a sample of a whole blood, plasma, serum or isolated corpuscles.

The biological liquid can be a sample of saliva.

The biological liquid can be a sample of urine.

For blood typing, the agglutination reagent may comprise monoclonal antibodies selected from the group consisting of blood group system antibodies (anti-A, anti-B and anti-D).

The continuous phase can be selected from the group consisting of hexadecane, Fluorinert and mineral oil.

The method may comprise introducing into the microfluidic reaction channel two reference droplets having the same volume.

The sequence of test droplet can be introduced into the microfluidic reaction channel after the second reference droplet has traveled a distance of from 10 to 20 widths of microfluidic reaction channel.

The test droplets may have a size of from 3 to 4 widths of the microfluidic reaction channel.

The distance between the test droplets introduced to the microfluidic reaction channel can be from 2 to 5 widths of the microfluidic reaction channel.

BRIEF DESCRIPTION OF THE DRAWINGS

The method is presented by means of exemplary embodiments on a drawing, in which.

DETAILED DESCRIPTION

The method presented herein involves detecting of agglutination by measuring a change in hydrodynamic resistance of biological liquid samples containing antigens, such as human and animal bodily fluids, e.g. blood. In particular, the method involves analysis of biological liquid samples after they have been removed from the body and they are not supposed to be reintroduced to the body. This method is especially suitable for conducting ordinary agglutination assays as well as for performing the agglutination analysis where only a small sample amount is available or where the use of other assay methods might bring a misleading result. Owing to its sensitivity, the method may be also used to confirm results obtained by different methods.

The method is suitable for detection of agglutination, i.e. the reaction occurring in a mixture containing specific antigens and antibodies. The method is useful especially for blood typing, cross-matching, direct Coombs test (DCT)/direct antiglobulin test (DAT) and indirect Coombs test/indirect antiglobulin test (IAT), or may serve as an individual test for detection of presence of other antibodies or may indicate infection, both bacterial and viral, or even an autoimmunological disease (e.g. Hashimoto's thyroiditis).

The method presented herein is preferably performed in a room temperature; however, it may be also conducted in lower or higher temperatures.

Figure 1:
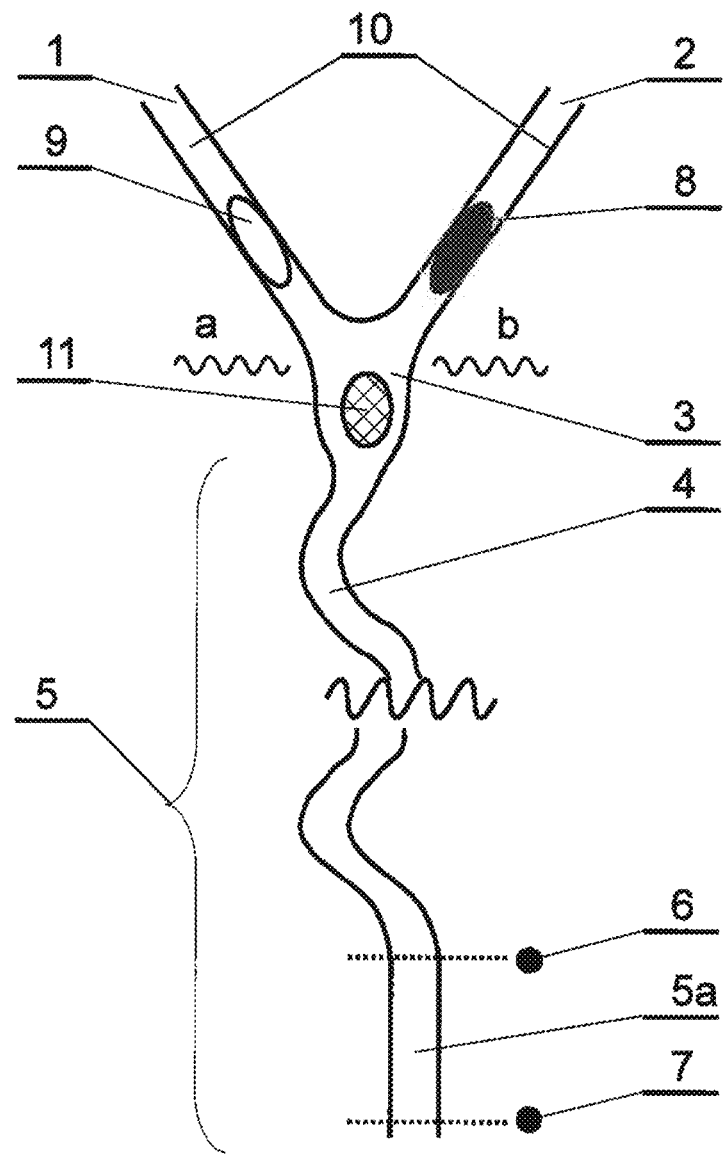
FIG. 1 is a schematic representation of a microfluidic device.

The method may utilize different microfluidic systems having an architecture, which is suitable for merging certain volume of a sample substance with certain volume of a reagent substance. For instance, an assay may be conducted with a microfluidic device as shown in FIG. 1. Other devices can be used as well, e.g. such as described in the Polish patent application PL396494. However, the microfluidic device to be utilised for determination of a change in hydrodynamic resistance must be depleted of capillaries that maintain the constant hydrodynamic resistance of the microfluidic channels. Thereby, the microfluidic device can be utilized to perform the measurement of change in hydrodynamic resistance, according to present invention.

The device shown in FIG. 1 has inlet channels 1, 2 for introducing droplets of sample substance 8 and reagent substance 9, which are suspended in a continuous liquid 10 which does not mix with the substances 8, 9 and a reaction channel 5. For example, the liquid 10 may be any liquid which does not mix with water solutions, such as oil from the group of simple hydrocarbons or functionalized hydrocarbons, mineral oil, fluorized oil or other. The inlet channels 1, 2 preferably join to form a single reaction channel 5, preferably preceded by a merging region 3, where the droplets 8, 9 may be joined to form a droplet 11 being a mixture of the sample substance and of the reagent substance. Optionally, at the merging region 3 there can be positioned—inside or outside the device—two electrodes (a, b) to enhance mixing of droplets by a pulse of oscillating electric field (electrocoalescence). The reaction channel 5 may comprise a meander portion 4, or preferably all reaction channel 5 to be meandering channel 5 which facilitates mixing of the droplet's components during flowing through the reaction channel 5. The mixed droplet(s) flow(s) to a section 5a which comprises two detectors 6, 7 positioned at a considerable distance from each other for measuring the time of flow of the droplet(s) through the section 5a of the outlet channel 5. The detectors 6, 7 may be e.g. optical or electrical detectors Thus, the section 5a is a measurement section 5a of the reaction channel 5.

To perform a test, the inlet channels 1, 2 are filled with the continuous phase 10 which is hydrophobic. The continuous phase 10 of the first inlet 1 channel is, preferably, the same substance as of the second inlet channel 2. The continuous phase and the liquid sample to be investigated have to be immiscible. The continuous phase 10 is hydrophobic, for the analyzed material to be hydrophilic (substantially bodily fluids are water solutions). The investigated sample can be a different liquid substance comprising antigen. The microfluidic channel may have, for example, rectangular, square, circular or oval cross-section, and preferably a square cross-section. The channel walls, preferably, also should be hydrophobic to ensure that the continuous phase will form a thin film separating the droplet from the walls. It eliminates the risk of contamination of the microfluidic device caused by biological material, thus the device can be considered as sterile.

The method for determining the agglutination by measuring the change in hydrodynamic resistance involves the following steps:

filling the microfluidic device with a continuous phase;
providing into the reaction channel 5a first reference droplet, i.e. the droplet comprising a predetermined volume of the liquid sample and a predetermined volume of the saline. The first reference droplet does not contain any reagent that might cause the agglutination, thereby assuring that the agglutination will not occur in the first reference droplet;

measuring the time of flow of the first reference droplet through the measurement section 5a of the reaction channel 5;

after the first reference droplet leaves the reaction channel 5, providing into the reaction channel a second reference droplet which is substantially, and preferably exactly, the same as the first reference droplet: having the same composition (i.e. the second reference droplet having the same liquid sample of the same volume, and the same volume of the same saline as the first reference droplet). The second reference droplet does not contain any reagent that might cause the agglutination, thereby, assuring the agglutination will not occur in the second reference droplet;

following the introduction into the reaction channel 5 of the second reference droplet, providing into the reaction channel 5 a sequence of test droplets, the sequence comprising, substantially, from 1 to 1000 of the test droplets. Test droplets are the droplets if liquid sample containing the reagent, i.e. monoclonal or polyclonal antibody that can cause the agglutination in the test droplet, in case the specific antigen is present in the liquid sample. All test droplets in the sequence being substantially, and preferably exactly, the same, i.e. all the test droplets have the same composition, the same liquid sample, the same known reagent, and being of the same volume. Moreover, the liquid sample of each test droplet is the same as the liquid sample contained in the first and second reference droplet. Thus, within one measurement each droplet, either reference or test provided into the reaction channel, contains the same liquid sample;

measuring the time of flow of the second reference droplet through the measurement section 5a of the reaction channel 5;

calculating hydrodynamic resistance of the reaction channel 5 during flow of the first reference droplet on the basis of the measured time of flow of the first reference droplet through the measurement section 5a of the reaction channel 5;

calculating hydrodynamic resistance of the reaction channel 5 during flow of the second reference droplet together with the sequence of the test droplets (having from 1 to 1000 test droplets) on the basis of the measured time of flow of the second reference droplet through the measurement section 5a of the reaction channel 5;

determining whether the agglutination occurred or not by comparing the obtained results. If agglutination occurs in the sequence of test droplets, then the flow of the test droplet(s) (together with the second reference droplet) causes increase of hydrodynamic resistance of the microfluidic channel (reaction channel 5) as compared to the calculated resistance of this channel during flow of the non-agglutinated droplets (i.e. the sequence of non-agglutinated sequence of test droplets). What is being compared is the value of the hydrodynamic resistance, calculated as described below, for a) first reference droplet and b) second reference droplet and a sequence ("train") of test droplets flowing after the second reference droplet.

The following describes the method for determination of agglutination according to the invention in greater details:

Following the filling of microfluidic channels 1, 2, 5 with continuous phase, a known volume of a liquid sample, e.g. in the amount of 60 nl-1,5 μl, is introduced into the first inlet channel 1, for example via a sample port. The surface tension between the liquid sample and the continuous phase keeps the provided sample in a shape of a droplet 8 so that it will not mix with the continuous phase 10 in the channel.

In case of a blood assay, the blood sample to be investigated can be whole (non-centrifuged) blood, drawn by using a suitable, known in the art method. For example, the blood sample can be drawn onto an anticoagulant deposit. Depending on the method of drawing and the type of the container (e.g. a tube) the following substances are suitable to be used as the anticoagulant: ethylenediaminetetraacetic acid (EDTA) or its sodium salt-disodium EDTA (EDTA-$Na_2$), trisodium citrate or citric acid, sodium oxalate or potassium oxalate, heparin (as a sodium, lithium or calcium salt). Nonetheless, the method presented herein is applicable regardless of a deposit onto which blood was collected.

The droplet of a liquid sample 8 of a predetermined volume is introduced into the inlet channel 2 and flows downstream this channel 2. The droplet of saline 9 of predetermined volume is introduced into the inlet channel 1 and flows downstream in the channel 9. The droplet of the liquid sample and the droplet of the saline are merged at the merging region 3, thereby forming a first reference droplet of a predetermined volume. The formed first reference droplet is introduced into the reaction channel 5 and flows downstream through the reaction channel 5, which is preferably meandered to provide better mixing of the droplet's components. The detectors 6, 7 measure the time of flow of the first reference droplet through the measurement section 5a of the reaction channel 5. The length of the measurement section 5a is preferably 10 cm. It is important that the first reference droplet is the only droplet present in the reaction channel 5 during the measurement of the time of flow of the first reference droplet. This measurement serves as calibration measurement which is taken into account in the calculations described below in details.

After the first reference droplet leaves the reaction channel, the second reference droplet is introduced into the reaction channel 5. As already mentioned, the second reference droplet should be of the same composition and of the same volume as the first reference droplet. Therefore, the second reference droplet is exactly the same as the first reference droplet. The second reference droplet may be generated for example in the same way as the first reference droplet.

Following the introduction into the reaction channel 5 the second reference droplet, the sequence of test droplets comprising, preferably form 1 to 1000 test droplet(s) is introduced into the reaction channel 5, therefore, the sequence of test droplets follows the second reference droplet flowing downstream through the reaction channel 5. Thus the second reference droplet together with the sequence of the test droplets form a series of droplets flowing in the same direction through the reaction channel 5. The distance between respective droplets in the series should be selected so as to assure separation of the droplets from each other over the entire length of the reaction channel 5 during flow of the series of droplets through the reaction channel 5.

While a series of droplets flows through the reaction channel 5, the time of flow of the second reference droplet through the measurement section 5a is measured. This means that during measurement of the time of flow of the second reference droplet, through the measurement section 5a, the series of droplets (the second reference droplet and the sequence of test droplets, i.e a predetermined number of the test droplets) is present in the reaction channel 5.

The test droplet(s), to be introduced into reaction channel 5 after the second reference droplet, may be generated as follows:

A known volume of the liquid sample 8, the same as the liquid sample of first and second reference droplet, is introduced into the inlet channel 2 The known volume of the reagent 9, comprising monoclonal or polyclonal antibody, is inputted into the device via second inlet channel 1. The reagent 9 flows along the second inlet channel 2 to be merged, at the merging region 3 with the sample 8, thereby forming a test droplet 11, at the merging point 3. However, the reagent 9 may be introduced into the merging region in a different way, for example the reagent 9 may be deposited within the merging region 3.

The water affinity of the reagent 9 and the sample 8 should be similar or preferably the same. The reagent may comprise a monoclonal or polyclonal antibody, for example, anti-A, anti-B or anti-D or other, and should be capable of causing an agglutination reaction with the antigen if present in the sample (specificity).

Optionally, following the introduction of a predetermined sample volume into the inlet channel 1, the sample 8 may by divided by generating a sequence of droplets, each of the same volume, preferably in a range of from 60 to 300 [nl], and more preferably each having a volume of 64 nl. Each droplet of the sample is to be merged with the droplet of a reagent containing the same, known, either monoclonal or polyclonal antibody.

The formed sequence of sample droplets flows downstream direction so that they are merged, one by one, with the predetermined volumes (droplets) of the same reagent 9 at the merging region 3 of the microfluidic system to form a sequence of test droplets. Each test droplet flows downstream direction through the reaction channel 5 of the microfluidic device.

The reaction channel 5 is provided with detectors 6, 7 spaced at the certain distance of the reaction channel 5, defining the measurement section 5a of the reaction channel 5. Preferably the reaction channel 5 is substantially long and shaped with plurality of meander so as the reaction channel 5 together with measurement section 5a of reaction channel 5 is meandering channel. The detectors 6, 7 measure the time of flow of each reference droplet flowing through the distance of measurement section 5a. The obtained data are further utilized for calculation of hydrodynamic resistance of the entire system, i.e. hydrodynamic of the reaction channel with hydrodynamic resistance of the flowing droplet(s) Preferably, the volume of the reference droplets and the test droplet(s) is preferably chosen so that each droplet is 3 to 4 times longer than the channel width.

The following presents the step of performing the measurement:
1. generation of a first reference droplet by merging the sample droplet with the saline or PBS serving as a marker
2. measurement of time of flow of the first reference droplet through the measurement section 5a of the reaction channel 5 and calculation of hydrodynamic resistance of the first reference droplet ($r_d$) together with resistance of a channel (R): $r_d+R$
3. generation of a second reference droplet, exactly the same as the first reference droplet, and then, after the second reference droplet has traveled a certain distance of about 10 to 20 channel widths (which is particularly useful to achieve the lack of interaction between the reference droplet and tests droplets), generation of a sequence of n test droplets (where n ∈ (1, 1000)) containing the liquid sample and a certain reagent; the droplets should be 3-4 times longer (such length of droplet features the highest sensitivity to changing the viscosity) than the channel width and separated from each other by 2-5 times the channel width (to achieve the safe distance between droplets which prevents collisions (from one side), and simultaneously to cause the increase of the interaction between droplets (from other side)), 4. measurement of the time of flow of second reference droplet through the measurement section 5a of the reaction channel 5 and calculation their hydrodynamic resistance together with resistance of a channel $(R+r_d+nr_n)$, 5. comparison of the time of flow of the second reference droplet with the time of flow of the first reference droplet enables calculation of the ratio $nr_n/(R+r_d)$.

Steps 3, 4 and 5 should be repeated as many times as a number of individuals to be detected. Because each sequence of test droplets comprises the same reagent, the steps 3, 4 and 5 should be repeated for different known reagents. In this procedure each sequence of droplet should be similar, i.e. the same number of droplets in the sequence, the same volume of the liquid sample and the same volume of the reagent in the test droplet(s), but each sequence of test droplet(s) having different known reagent (e.g. different monoclonal or polyclonal antibody).

Figure 2A:
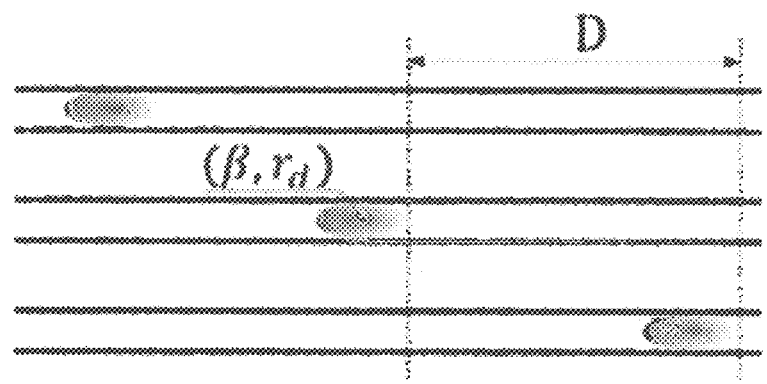
FIG. 2A-2B is a schematic representation useful for calculations of change in hydrodynamic resistance of tested liquid sample.
Figure 2B:
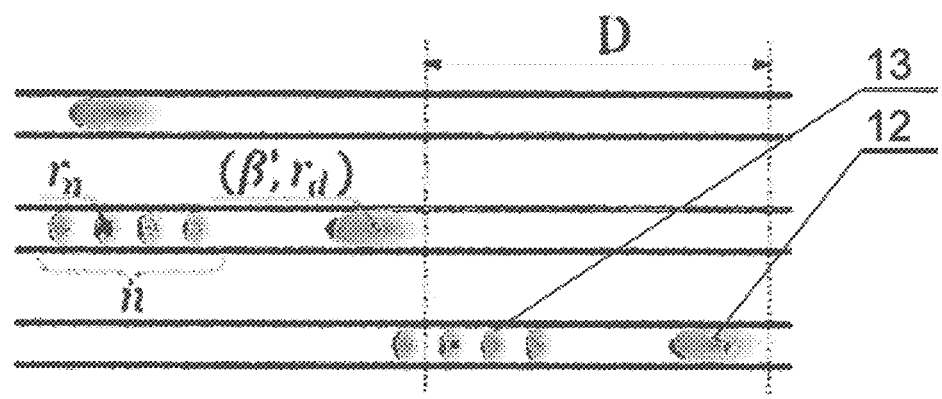

FIG. 2A-2B is a schematic representation useful for calculations of change in hydrodynamic resistance of single droplet (FIG. 2A), and a sequence of droplets (FIG. 2B).

The flow time of a single droplet (i.e. the second reference droplet) 12 at the presence in the reaction channel 5 the sequence of test droplets 13, at the distance D measured by the detectors fixed at checkpoints, gives data used to calculation of hydrodynamic resistance.

The second reference droplet is introduced to the channel after the first reference droplet has left the channel, such as not to influence the flow of the first reference droplet by the second reference droplet.

The first reference droplet flow time through the measurement section 5a of the reaction channel 5 depends on its endogenous viscosity, while the flow time of the droplet depends on the endogenous viscosity and the change of its viscosity brought about by reaction with the agglutination reagent.

By comparing the hydrodynamic resistance of the system (i.e. reaction channel+respective droplet(s)) information is obtained about the presence of an antigen in the tested sample.

The hydrodynamic resistance is calculated by using the following formulas:

$$\beta = \frac{v_l}{\overline{V}} = \frac{DS}{Q(t_2 - t_1)} \quad \text{(formula I)}$$

$$R + r_d = \frac{p}{Q} = \frac{p\beta(t_2 - t_1)}{DS} \quad \text{(formula II)}$$

$$R + nr_n + r_d = \frac{p\beta(t'_2 - t'_1)}{DS} \quad \text{(formula III)}$$

$$\frac{nr_n}{R + r_d} = \frac{(t'_2 - t'_1)}{(t_2 - t_1)} - 1 \quad \text{(formula IV)}$$

wherein:
β—mobility of the reference droplet
$v_l$—linear velocity of a droplet
$\overline{V}$—average velocity of the continuous phase
$nr_n$—hydrodynamic resistance of sequence of analyzed droplets
$t_1$—time of detection of the first reference droplet under the first detector
$t_2$—time of detection of the first reference droplet under the second detector
$t_1'$—time of detection of the second reference droplet under the first detector
$t_2'$—time of detection of the second reference droplet under the second detector
D—distance between detectors
R—hydrodynamic resistance of a channel
S—area of the channel cross-section
$r_d$—hydrodynamic resistance of a single droplet
Q—volumetric rate of flow in a channel
p—pressure inducing the flow Having given the time of flow of the first reference droplet, form formula I can be used for calculation of the mobility of the reference droplet (β), as D (distance between detectors), S (area of the channel cross-section) are known values. Moreover, Q (volumetric rate of flow in a channel)—is calculated by weighing the liquid flowing out from the chip onto a balance in the fixed time and calculating Q as a ratio of the volume of the flown out liquid (calculated based on the weight) and time.

Next the values of $t_1$ and $t_2$—measured for the first reference droplet, and values $t_1'$, $t_2'$ measured for second reference droplet can by utilized for calculation of the hydrodynamic resistance of the system by using of formula II—for the calculation of hydrodynamic resistance of the system during flow of this droplet, and by using formula III—for calculation of the hydrodynamic resistance of the system during flow of the series of droplets consisting of the second reference droplet and the sequence of test droplets.

The pressure inducing the flow (p) constitutes the difference in pressure over the reservoir with the continuous phase (oil), and the atmospheric pressure. The reservoir of constitutes phase is a dispenser that introduces the continuous phase into the microfluidic device.

In the next step calibration is performed. The calibration is performed for variety of sequences of test droplets, i.e. the sequences of agglutinated test droplets and non-agglutinated test droplets of known viscosity. The calibration is performed as follows. Sequences of droplets are generated comprising various number n of droplets, for example for n from 1 to 100. One type of sequences is generated with droplets with agglutination and another type of sequences is generated with droplets without agglutination. As a result of calibration, the values of hydrodynamic resistance can be obtained, related to the given sequences of droplets. These values may be subject to some standard error (deviation). The calibration allows to determine, for which minimal number n of droplets it is possible to distinguish the value of hydrodynamic resistance of a sequence of droplets in which agglutination occurred and of a sequence of droplets in which agglutination did not occur. The calibration provides device-specific results, dependent e.g. on its structure and configuration of input channels and valves.

The calibration gives the information of the lowest number of test droplets n that should be generated as one sequence of test droplets to be introduced into the reaction channel 5 after the second reference droplet in order to be able to distinguish the sequence in which the agglutination occurred from these where agglutination did not occur.

The results of tests that have been performed show that one hundred percent (100%) reliable distinction can be obtained for the sequence of test droplets having three test droplets (n=3) that flow after the second reference droplet in the reaction channel 5. The term: 'one hundred percent reliable distinction' is understood as a sum of tripled average standard deviations measured for 100 agglutinated test droplets and 100 non-agglutinated test droplets, respectively.

Nonetheless, for some measurement, the sequence of test droplet may consists of one test droplet (n=1) giving reliable distinction between calculated hydrodynamic resistance for the agglutinated and non agglutinated droplet series.

The measurements for the first reference droplet are performed to determine the hydrodynamic resistance of this droplet. However, it is not necessary to determine the exact value of the hydrodynamic resistance, but it is enough to determine how much the resistance of the system has changed with respect to the flow of the continuous phase. It shall be noted that the increase of the hydrodynamic resistance of the system (i.e. flow of the continuous phase with the droplet) usually causes reduction of the volumetric rate of flow. Moreover, the measurement of the first reference droplet can be treated as a calibration measurement. Next, a second reference droplet is introduced, which is followed by a sequence of test droplets for which the hydrodynamic resistance is to be calculated. The particular distance between the second reference droplet and the test droplets is fixed in order to reduce interactions between the sequence of test droplets and the second reference droplet (such interactions could cause false results). As mentioned herein, each droplet changes the hydrodynamic resistance of the system, and this influences the volumetric rate of flow of the continuous phase. On the other hand, the change of the volumetric rate of flow is visible in the whole system; therefore the second reference droplet detects the presence of additional droplets by changing its velocity. The change of the velocity of the second reference droplet and comparison of the velocity of the second reference droplet and the first reference droplet (introduced individually into the system) allows to calculate the change of the hydrodynamic resistance introduced to the system by the test droplets.

When the test droplets move in a sequence, they form a kind of a "train" (sequence) and influence on each other. Measurements have shown that this influence increases (or sometimes decreases) the hydrodynamic resistance of measured liquids, which is beneficial for the measurement.

The following describes exemplary stages of blood typing with the use of the hydrodynamic resistance measurements:
1. Filling the channels with the continuous phase.
2. Introduction of a sample (1-1.5 µl) into the inlet channel.
3. Division of a sample by generating a sequence of 3 droplets, 250 nl each.
4. Generation of a first reference droplet comprising saline/PBS (312 nl) and the sample (250 nl)
5. Measurements of hydrodynamic resistance of first reference droplet.
6. Generation of a second reference droplet comprising saline/PBS (312 nl) and the sample (250 nl, and then the test droplet comprising reagent (64 nl) with monoclonal antibodies (anti-A) merged the first blood droplet.
7. Measurements the time of flow of second reference droplet flowing with test droplet through the channel, and then calculation of hydrodynamic resistance in the microfluidic channel during the movement of analysed droplets.
8. Generation of a second reference droplet comprising saline/PBS (312 nl) and sample (250 nl) and then a test droplet comprising a reagent (64 nl) with monoclonal antibodies (anti-B), other than in the previous step, merged with the second blood droplet.
9. Measurements of time of flow of the second reference droplet during the movement of analysed droplets and calculation of hydrodynamic resistance of the microfluidic channel.
10. Generation of a second reference droplet comprising saline/PBS (312 nl) and sample (250 nl) and then a test droplet comprising a reagent (64 nl) with monoclonal antibodies (anti-D), other than in the previous step, merged with the second blood droplet.
11. Measurements of time of flow of the second reference droplet during the movement of analysed droplets and calculation of hydrodynamic resistance of the microfluidic channel
12. Determination whether agglutination occurred in individual test droplets or not by comparison of the hydrodynamic resistance during their flow through the microfluidic channel with the resistance in the microfluidic channel during the flow of the reference droplet.

An external factor which influences directly on the time of flow is the geometry of a channel, in particular:
i) the cross section of a microchannel, preferable rectangular, with aspect ratio of sides 1:3 or 1:4,
ii) the length of a part of the microfluidic channel in which the measurements are being performed, and also
iii) the viscosity of continuous phase,
iv) iv) the presence or absence of surfactant in/or both phases or
v) the flow rate of the continuous phase.

All of these parameters must be fixed arbitrarily. Nonetheless, the initial conditions are supposed to be set so that the whole procedure—from introducing the sample to the result readout—takes short time, approximately a few minutes.

For the purposes of tests before transfusion the number of steps in which droplets with blood samples are generated and merged with reagents must be increased by the number of additional antigens being detected. This applies in hydrodynamic method for detection of agglutination.

Instead of whole blood one can use standardized red blood cells with certain (known) antigens on their surface. Monoclonal reagents must therefore be replaced by patient's serum or plasma so that the test will show the presence of antibodies in their blood. This variant may be a part of blood typing or cross-testing procedure, or serve as an individual test for detection of other antibodies, presence of which may indicate infection, both viral and bacterial, or even an autoimmunological disease (e.g. Hashimoto's thyroiditis).

The following describe the exemplary stages of direct Coombs test (DCT)/direct antiglobulin test (DAT) with the use of the hydrodynamic resistance measurements:
1. Filling the channels with the continuous phase.
2. Introduction of a sample (0.5-1 µl) into the inlet channel.
3. Division of the sample by generating a sequence of 2 droplets, 250 nl each.
4. Generation of a droplet of saline/PBS (64 nl) and merging with the first blood droplet in the chamber—first reference droplet.
5. Measurements the time of flow and calculation of the hydrodynamic resistance of this first reference droplet in the microfluidic channel during its movement.
6. Generation of second reference droplet, exactly the same as the first reference droplet, and generation of a droplet of an antiglobulin serum (Coombs reagent) (64 nl) and merging with the second blood droplet in the chamber—test droplet.

7. Measurements of time of flow of second reference droplet during movement of the second reference droplet and the test droplet through the channel and calculation of the hydrodynamic in the microfluidic channel during the movement of this droplets.

8. Determination whether agglutination occurred in the test droplet or not by comparison of its hydrodynamic resistances with the hydrodynamic resistance of the reference droplet.

Preferably, hexadecane is used as a continuous phase. Fluorinert (e.g. FC40, HFE-7500), which is commonly used in microfluidic techniques for biochemical applications, can be also used, as well as other mineral oils. The choice of oil should be based on the wettability of a material the channels will be made of and on the surface tension between considered oil and analyzed material.

Any physicochemical interactions between the continuous phase and the material of microfluidic channel is made of disqualify such a combination. For example, some elastic polymers, such as polydimethylsiloxane (PDMS), swell upon contact with any oil. This results in shortening of their working life and remarkably limits the spectrum of applications in which such material can be used.

The biocompatibility of the continuous phase and the material of the microfluidic channel is an important issue. A preferred material for microfluidic channel is polycarbonate, primarily because of its relatively low price and ease of processing. Furthermore, there is a specific procedure developed for hydrophobisation of its surface. The translucency of a chosen material is also important. The microfluidic channel does not have to be completely transparent, however it should enable an optical analysis of the inside of at least key parts of the channel, i.e. the checkpoints (at least two) at which the detectors are arranged. Also polylactide (PLA) may be used as a material for microfluidic channel due to its transparency, hydrophobicity, biocompatibility and biodegradability.

Preferably, the channel has a rectangular or square cross-section. It is more favorable than the circular cross-section due to an arrangement of eddy pairs appearing inside flowing droplets. In a droplet flowing through a square or rectangular channel, the eddy pairs arrange in such a way that the mixing of its content is enhanced. These whirls are also corresponsable for gathering of aggregates, such as agglutinates (antigen-antibody complexes), in the rear or fore part of a droplet. This enables another (confirmative) method for detection of agglutination—by measurements of the intensity of light passing through a droplet or by comparing contrast between analyzed droplets of a certain sample.

Figure 3:
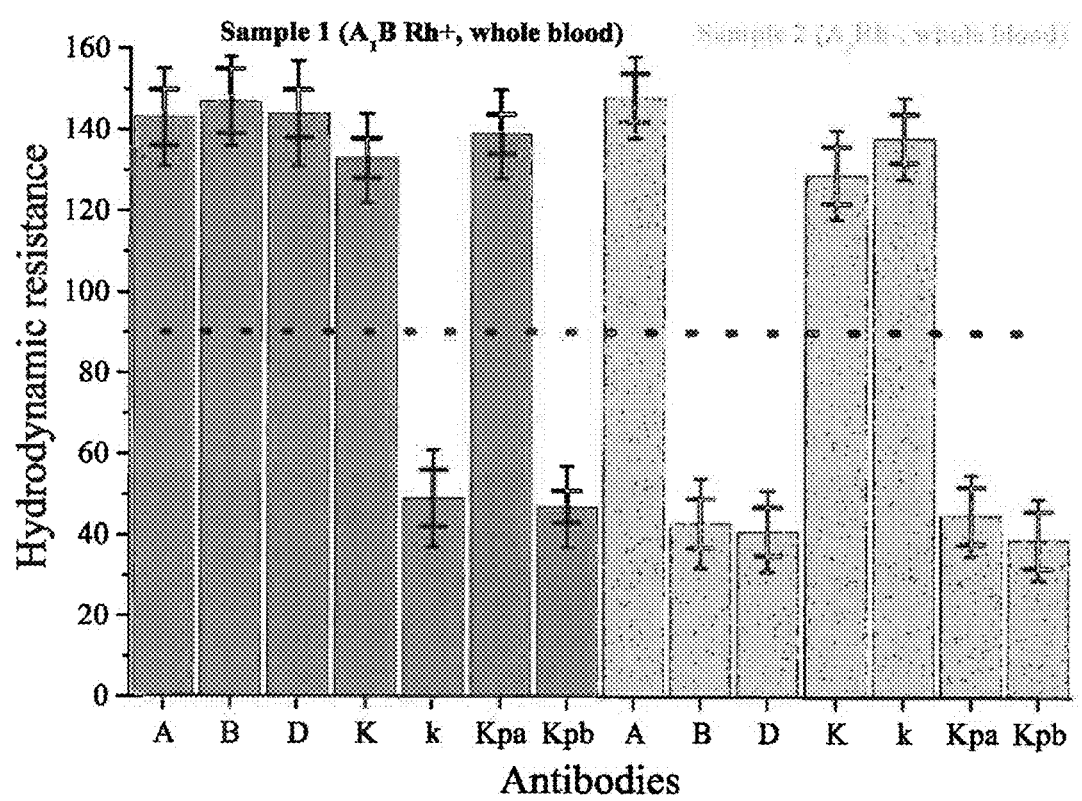
FIG. 3 presents the results of measurements of hydrodynamic resistance of certain droplets containing samples and reagents.

An example of such a distinction is presented in FIG. 3. The intensity of light is converted into amplitude of voltage by a light-to-voltage converter. The droplet without agglutination is homogenous, in contrast to the droplet of the sample with agglutination. The process of agglutination and further accumulation of aggregates in the rear of a droplet results in a non-homogenous distribution of droplet's content. Any discrepancy between the analyzed droplet and the baseline assigned to a homogenous droplet indicates a reaction taking place inside.

The length of the channels is of minor importance. It should enable proper and sufficient mixing of droplets content. This can be influenced either by its length or the shape of windings. Preferably, both of these features may be combined to obtain the best effect.

The droplet volume may be adjusted according to the microfluidic channel width. Since the rheological method relies on the change in hydrodynamic resistance, it is desired to fix a volume for which that change is the most observable. For channels of square cross section and a width of 360 µm this effect is enhanced in droplets having the volume of 320 nl (as described in *Phys. Rev. Lett.*, 2012, 108, 134501S. Jakiela, P. M. Korczyk, S. Makulska, O. Cybulski and P. Garstecki,). Furthermore, for analyses of blood/red blood cells (RBC) samples in contact with monoclonal reagents/plasma/serum, the preferred proportion is 256 nl and 64 nl, respectively. These conditions provide the largest difference in mobilities of agglutinated and non-agglutinated droplets.

EXAMPLE

The test was performed with the use of the whole human blood as a sample, and commercially available monoclonal reagents (as used in analytical laboratories) as a reagent containing antibodies. The detection area comprised a 10 cm long channel equipped with two photo-diodes serving as optical detectors and checkpoints at once. The results of measurements of the hydrodynamic resistance are presented in FIG. 4. Typical hydrodynamic resistance is significantly different for agglutinated and non-agglutinated droplets. The difference reaches even 10% for human whole blood samples.

The error bars mark the average standard deviation for each sample, i.e. one $\sigma$ in normal distribution, and the triple $\sigma$ as well. There is no overlap of triple $\sigma$ from agglutinated and non-agglutinated samples. Thus the probability of a mistyping is practically zero. The sample with the worst precision has a multiple $\sigma$ value slightly above 4. That implicates the minimum reliability of these measurements to be higher than 99.9991% (1 mistake per 1 million tests).

The reliability of the bedside ABO agglutination tests performed with special cards may vary and is from 93% to 99% (when combined with another test). In case of weak A antigen ($A_2$) detection performed with cards the reliability falls below 40%. As it can be seen in FIG. 3 there is no significant difference in reliability of detection of this antigen using the rheological method comparing to $A_1$ detection. What is more, detection of antigens from the Kell system remains on the same high level of reliability.

The occurrence of ABO-incompatible transfusions is reported to range from 1 to 250 per 100 000 transfusion units. Incorrect typing (both technical and clerical errors) using standard methods constitutes about 13% of transfusion errors. The errors are due not only to the assaying technique, but often result also from mistakes in the procedure and from improper handling of samples.

What is important, the present method does not require preprocessing of blood such as centrifugation. Another advantage is the small amount of blood needed to perform the test. Standard methods require 5-15 ml of blood for the typing, and as much again for cross testing. In the hydrodynamic method only a microliter of blood or so is needed.

In tests such as PCR, LAMP or ELISA, the increasing number of polymer chains, DNA or other molecules inside a droplet should result in a measurable change in its hydrodynamic resistance. However, there is no conclusive data in the literature to confirm or deny this assumption.

The invention claimed is:

1. A method for determining agglutination of a tested biological liquid by measuring a change in a hydrodynamic resistance of the tested biological liquid flowing through a microfluidic reaction channel of a microfluidic device, the method comprising the steps of:

a) calibrating the microfluidic device by calculating a calibrated value of the hydrodynamic resistance of a sequence of droplets of a known biological liquid in which agglutination occurred and a calibrated value of a sequence of droplets of the known biological liquid in which agglutination did not occur, according to steps from (b) to (i) and next performing the steps from (b) to (i) for the tested biological liquid;

b) filling the microfluidic reaction channel with a hydrophobic continuous liquid phase, the microfluidic reaction channel having detectors spaced at a distance defining a measurement section of the microfluidic reaction channel, wherein the microfluidic reaction channel is configured such that the pressure inducing the flow in the microfluidic reaction channel is a difference between a pressure over the reservoir with the continuous phase and an atmospheric pressure;

c) introducing into the microfluidic reaction channel a first reference droplet being a droplet of the biological liquid merged with saline or PBS or water and immiscible with the continuous phase;

d) causing the first reference droplet to flow through the microfluidic reaction channel having a measurement section;

e) measuring a time of flow of the first reference droplet through the measurement section of the microfluidic reaction channel;

f) introducing into the microfluidic reaction channel a second reference droplet being the same as the first reference droplet, followed by a sequence of 1 to 1000 test droplets, wherein the test droplets comprise an agglutination reagent and the biological liquid which is the same as the biological liquid comprised in the first reference droplet and in the second reference droplet, and wherein the test droplets are immiscible with a continuous phase;

g) causing the second reference droplet and the sequence of the test droplets to flow through the microfluidic reaction channel;

h) measuring a time of flow of the second reference droplet through the measurement section while the sequence of the test droplets is present in the microfluidic reaction channel;

i) calculating the hydrodynamic resistance of the first reference droplet and of the second reference droplet being followed by the sequence of the test droplets, on the basis of the times of flow measured in steps (e) and (h); and j) comparing the value of the hydrodynamic resistance of the first reference droplet with the value of the hydrodynamic resistance of the second reference droplet being followed by the sequence of the test droplets, and determining that agglutination occurs in the sequence of the test droplets of the tested biological liquid if the value of the hydrodynamic resistance of the second reference droplet being followed by the sequence of the test droplets is increased as compared to the value of the hydrodynamic resistance of the first reference droplet.

2. The method according to claim 1 wherein the continuous phase separates the droplets from a wall surface of the microfluidic channel.

3. The method according to claim 1, wherein the continuous phase is selected from the group consisting of hexadecane fluorized oil and mineral oil.

4. The method according to claim 1, comprising introducing into the microfluidic reaction channel two reference droplets having the same volume.

5. The method according to claim 1, wherein the sequence of the test droplets is introduced into the microfluidic reaction channel after the second reference droplet has traveled a distance of from 10 to 20 widths of the microfluidic reaction channel.

6. The method according to claim 1, wherein the test droplets have a size of from 3 to 4 widths of the microfluidic reaction channel.

7. The method according to claim 6, wherein a distance between the test droplets introduced to the microfluidic reaction channel is from 2 to 5 widths of the microfluidic reaction channel.

8. The method according to claim 1, wherein the tested biological liquid is a sample of a whole blood, plasma, serum or isolated corpuscles.

9. The method according to claim 8, wherein for blood typing, the agglutination reagent comprises monoclonal antibodies selected from the group consisting of blood group system antibodies which are anti-A, anti-B and anti-D antibodies.

* * * * *